United States Patent [19]

Merger et al.

[11] Patent Number: 5,202,465

[45] Date of Patent: Apr. 13, 1993

[54] PREPARATION OF 2-METHYLENEPROPANE-1,3-DIOL DICARBOXYLATES

[75] Inventors: Franz Merger, Frankenthal; Tom Witzel, Ludwigshafen; Martin Brudermueller, Mannheim, all of Fed. Rep. of Germany

[73] Assignee: BASF Aktiengesellschaft, Ludwigshafen, Fed. Rep. of Germany

[21] Appl. No.: 904,925

[22] Filed: Jun. 26, 1992

[30] Foreign Application Priority Data

Jun. 26, 1991 [DE] Fed. Rep. of Germany ....... 4121048

[51] Int. Cl.$^5$ ............................................. C07C 67/02
[52] U.S. Cl. .................................... 560/261; 560/263
[58] Field of Search ................................ 560/261, 263

[56] References Cited

FOREIGN PATENT DOCUMENTS 1957996 6/1970 Fed. Rep. of Germany .
2003933 8/1971 Fed. Rep. of Germany .
2054987 5/1972 Fed. Rep. of Germany .
2054988 5/1972 Fed. Rep. of Germany .
2626173 12/1977 Fed. Rep. of Germany .
1942014 1/1979 Fed. Rep. of Germany .
3243545 5/1984 Fed. Rep. of Germany .
8703281 6/1987 PCT Int'l Appl. .
1037650 8/1966 United Kingdom .

OTHER PUBLICATIONS

JP 52 27 710 Chem Abstr. Feb. 3, 1977.
JP 47 28965 Chem Abstr Mar. 12, 1968.
Heterocycles, 14 (2), (1980), 189.
Angew. Chem., 79 (1967), 1.
J. Am. Chem. Soc., 76, 1954, p. 2285.
Bull. Soc. Chim. Fr. (1965) 1355.

*Primary Examiner*—Paul J. Killos
*Attorney, Agent, or Firm*—Herbert B. Keil

[57] ABSTRACT

2-Methylenepropane-1,3-diol dicarboxylates are prepared by reacting pentaerythritol tetracarboxylates on solid catalysts at elevated temperatures.

5 Claims, No Drawings

PREPARATION OF 2-METHYLENEPROPANE-1,3-DIOL DICARBOXYLATES

The present invention relates to a process for preparing 2-methylenepropane-1,3-diol dicarboxylates (1,3-diacyloxy-2-methylenepropanes) from pentaerythritol tetracarboxylates.

2-Methylenepropane-1,3-diol dicarboxylates are synthons with a wide variety of uses, inter alia 2-methylenepropane-1,3-diol diacetate being used to prepare 2-benzyl-4-hydroxymethylfuran (Elliott alcohol) (DE 35 46 371 A1, EP 187 345 A1). They can also be used to prepare pyrans (THL, 28 (1987) 6219), 1,3-dihydroxyacetone derivatives (DE 25 56 525 A1) or 3,5-dialkylpyridines (Liebigs Annalen Chem., (1973) 111).

Bull. Soc. Chim. Fr. (1965) 1355 describes the synthesis of 2-methylenepropane-1,3-diol from acrolein, cyclopentadiene and formaldehyde via 2,2-bis(hydroxymethyl)-5-norbornene. The same synthetic principle with anthracene in place of cyclopentadiene is disclosed in FR 1350723. Both processes entail a sequence of three reactions: Diels-Alder reaction, aldol Cannizarro and retro-Diels-Alder reaction.

Oxidation of isobutene in the presence of acetic acid on Pd-doped $Al_2O_3$ catalysts provides direct access to 2-methylenepropane-1,3-diol diacetate (eg. JP 52027710, JP 47028965, DE-A 19 42 014, DE-A 20 03 933). It is also possible to react esters of methallyl alcohol under the same conditions to give 2-methylenepropane-1,3-diol diacetate (e.g., DE-A 20 54 987, DE-A 19 09 964).

It is likewise known to convert methallyl chloride into the diacetate by chlorination, isomerization of the resulting olefin mixture on zinc(II) chloride and reaction with acetic acid/triethylamine (DE-A 32 43 545 A1).

2-Methylenepropane-1,3-diol is also a by-product of the alkali-catalyzed dehydrobromination of pentaerythritol monobromide in addition to the main product 3,3-bis(hydroxymethyl)oxetane (Heterocycles, 14 (2), (1980), 189). This heterolytic fragmentation is known in principle for 3-haloalkanols (Angew. Chem., 79 (1967), 1), especially for 1,3-diols (J. Am. Chem. Soc., 76 (1954), 2285), but has only limited preparative use because the yields are too low.

The disadvantages of the processes hitherto disclosed for preparing 2-methylenepropane-1,3-diol diacetate are thus, besides the very low yield in some cases, especially the multistage reaction sequence in the known processes, the high industrial costs, especially because of safety problems (oxidation), or the use of inconvenient starting materials.

It is an object of the present invention to provide a process for preparing 2-methylenepropane-1,3-diol dicarboxylates which is straight-forward to implement industrially and does not have the disadvantages indicated above.

We have found that this object is achieved by a process for preparing 2-methylenepropane-1,3-diol dicarboxylates of the formula I

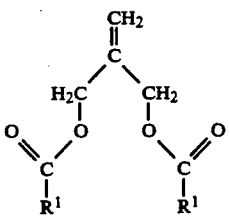

wherein $R^1$ is hydrogen or alkyl of 1 to 4 carbon atoms, which comprises reacting pentaeryrthritol tetracarboxylates of the formula II

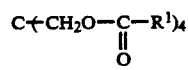

where $R^1$ has the abovementioned meaning, on solid catalysts at from 150° to 450° C., preferably 250° to 400° and especially 300° to 350° C., and under from 1 mbar to atmospheric pressure, preferably 50 to 500 mbar.

The starting material of the formula II can be obtained either commercially or in a conventional manner by esterification of pentaerythritol.

The pentaerythritol tetracarboxylates are preferably contacted as gases with the solid catalyst, the reaction being carried out batchwise or, in particular, continuously. The reaction can be carried out in a fixed bed or in a fluidized bed. The process is preferably carried out under reduced pressure.

It can also take place under protective gas, e.g., nitrogen or argon.

It is advantageous for the space velocity in the reaction to be from 0.01 to 20 g, in particular 0.1 to 5 g, of starting material of the formula II per g of catalyst and hour.

The pentaerythritol tetracarboxylates of the formula II can be introduced into the reactor as melts or dissolved in an inert solvent. Examples of suitable inert solvents are ethers such as THF and dioxane; aromatic hydrocarbons such as benzene, toluene and xylenes; aliphatic alcohols such as ethanol, methanol, n-propanol and isopropanol; aliphatic carboxylic acids such as acetic acid, propionic acid and butyric acid and mixtures of these solvents.

If the reaction is carried out in a fixed bed, it is preferable to arrange the fixed bed vertically and place inert materials over the catalyst. The starting materials are then introduced from above and heated to the reaction temperature in contact with the inert material.

The reaction products are trapped in a downstream, cooled receiver. The products are isolated from the reaction mixture by, for example, distillation; the by-products include formaldehyde and the acid eliminated from the particular ester. Unreacted starting materials can be recycled to the reaction.

Solid catalysts (heterogeneous catalysts) are used. Suitable examples are oxides of elements of main groups three and four and of transition groups two to six of the periodic table. Aluminum oxides, titanium oxides, zeolites and/or heteropolyacids, especially of tungsten and molybdenum, are preferred.

It is assumed that, in particular, acidic groups on the surface of the catalysts are beneficial for the course of the reaction. The catalysts can be used in the form of extrudates but also as beads, chips or powder.

EXAMPLES

Example 1

A melt of 30 g of pentaerythritol tetraacetate per hour was fed at 350° C. and under from 50 to 100 mbar onto a catalyst bed composed of 80 g of $Al_2O_3$ (1.5 mm extrudates) and, on top of this, a layer of silica beads in a heated silica tube (internal diameter 28 mm). The gaseous reaction products were condensed in a downstream cooled receiver.

After operation for 1 hour, 3.5 g of 2-methylenepropane-1,3-diol diacetate were isolated.

The yield was 21 % of theory based on pentaerythritol tetraacetate.

Example 2

70 g per hour of a solution of 31% by weight of pentaerythritol tetraacetate in toluene were fed at 300° C. and under 470 mbar onto a catalyst bed composed of 75 g of $Al_2O_3$ (1.5 mm extrudates) and, on top of this, a layer of silica beads in a heated silica tube (internal diameter 30 mm). After running for 2 hours, 11 g of 2-methylenepropane-1,3-diol diacetate had condensed.

The yield was 46% of theory based on pentaerythritol tetraacetate.

Example 3

80 g per hour of a solution of 29% by weight of pentaerythritol tetraacetate in acetic acid were fed at 350° C. and under 170 mbar onto a catalyst bed composed of 60 g of $Al_2O_3$ (1.5 mm extrudates) and, on top of this, a layer of silica beads in a heated silica tube (internal diameter 50 mm). After running for 5 hours, 25.7 g of 2-methylenepropane-1,3-diol diacetate had condensed.

The yield was 38% of theory based on pentaerythritol tetraacetate.

Example 4

30 g per hour of a solution of 30% by weight of pentaerythritol tetraacetate in glacial acetic acid were fed at 300° C. and under 400 mbar onto a catalyst bed composed of 260 g of $Al_2O_3$ (as 1.5 mm chips) and, on top of this, a layer of silica beads in a heated silica tube (internal diameter 30 mm). After running for 2 hours, 2.7 g of 2-methylenepropane-1,3-diol diacetate had condensed.

The yield was 26% of theory based on pentaerythritol tetraacetate.

Example 5

42 g per hour of a solution of 30% by weight of pentaerythritol tetraacetate in glacial acetic acid were fed at 350° C. and under 300 mbar onto a catalyst bed composed of 62 g of $TiO_2$ (as 1.5 mm extrudates) and, on top of this, a layer of silica beads in a heated silica tube (internal diameter 30 mm). The reaction ran for 2 hours.

The yield of 2-methylenepropane-1,3-diol diacetate was about 10% of theory based on pentaerythritol tetraacetate.

We claim:

1. A process for preparing 2-methylenepropane-1,3-diol dicarboxylates of the formula I

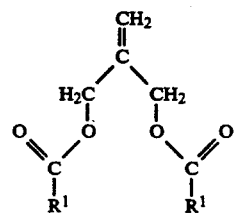

where $R^1$ is hydrogen or alkyl of 1 to 4 carbons, which comprises reacting pentaerythritol tetracarboxylates of the formula II

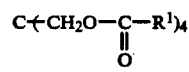

where $R^1$ has the abovementioned meaning, on solid catalysts at from 150° to 450° C. and under from 1 mbar to atmospheric pressure.

2. A process as claimed in claim 1, wherein the reaction is carried out at from 250° to 400° C. and under from 50 to 500 mbar.

3. A process as claimed in claim 1, wherein the solid catalysts are oxides.

4. A process as claimed in claim 3, wherein aluminum oxides, titanium oxides, zeolites or heteropolyacids or mixtures of these substances are employed as catalysts.

5. A process as claimed in claim 1, wherein R is methyl.

* * * * *